United States Patent
Huang et al.

(10) Patent No.: US 12,303,223 B2
(45) Date of Patent: May 20, 2025

(54) SLAVE-SIDE PROPELLING DEVICE AND CONTROLLING METHOD FOR INTERVENTIONAL SURGICAL ROBOT

(71) Applicant: BEIJING WEMED MEDICAL EQUIPMENT CO., LTD, Beijing (CN)

(72) Inventors: Tao Huang, Beijing (CN); Jing Xie, Beijing (CN)

(73) Assignee: BEIJING WEMED MEDICAL EQUIPMENT CO., LTD, Beijing (CN)

( * ) Notice: Subject to any disclaimer, the term of this patent is extended or adjusted under 35 U.S.C. 154(b) by 1156 days.

(21) Appl. No.: 17/037,567

(22) Filed: Sep. 29, 2020

(65) Prior Publication Data

US 2021/0007816 A1     Jan. 14, 2021

Related U.S. Application Data

(63) Continuation of application No. PCT/CN2020/097078, filed on Jun. 19, 2020.

(51) Int. Cl.
| | |
|---|---|
| *A61B 34/35* | (2016.01) |
| *A61B 34/00* | (2016.01) |
| *A61B 34/30* | (2016.01) |
| *A61B 34/37* | (2016.01) |

(52) U.S. Cl.
CPC .............. *A61B 34/35* (2016.02); *A61B 34/37* (2016.02); *A61B 34/71* (2016.02); *A61B 2034/301* (2016.02)

(58) Field of Classification Search
CPC .............. A61B 34/30; A61B 2034/301; A61B 2034/303; A61B 34/37; A61B 34/71
See application file for complete search history.

(56) References Cited

U.S. PATENT DOCUMENTS

2013/0066304 A1\*   3/2013   Belson .................. A61B 34/37
                                                                               606/1

FOREIGN PATENT DOCUMENTS

| CN | 108309370 A | \* | 7/2018 | ....... A61B 17/00234 |
|---|---|---|---|---|
| JP | 2018019987 A | \* | 2/2018 | |

OTHER PUBLICATIONS

English Language Translation of CN108309370A, Shen et al., Jul. 24, 2018. Espacenet Global Dossier. (Year: 2018).\*
English Language Translation of JP2018019987A, Guo et al., Feb. 8, 2018. Espacenet Global Dossier. (Year: 2018).\*

\* cited by examiner

*Primary Examiner* — Tan-Uyen T Ho
*Assistant Examiner* — Cherie M Poland
(74) *Attorney, Agent, or Firm* — Hemisphere Law, PLLC; Zhigang Ma

(57) ABSTRACT

A slave-side propelling device for an interventional surgical robot and a controlling method for the device are provided. The rubbing part, the clamping part, the catheter rotating part and the moving stepping motor part are installed and fixed on the housing. The transmission part is configured to transmit the torque of the moving stepping motor part to the sliding part and the pushing part. The sliding part is configured to drive the guide wire to reciprocate. The pushing part and the clamping part cooperate to clamp or loosen the guide wire. The rubbing part is configured to drive the guide wire to rotate. The catheter rotating part is configured to clamp the catheter and push the catheter into or withdraw the catheter out of the blood vessel.

5 Claims, 9 Drawing Sheets

SLAVE-SIDE PROPELLING DEVICE AND CONTROLLING METHOD FOR INTERVENTIONAL SURGICAL ROBOT

TECHNICAL FIELD

This disclosure relates generally to minimally invasive vascular interventional surgery, and more specifically to a control technology of a catheter and guide wire in a slave-side propelling of a robot in interventional surgery, namely, a slave-side propelling device and controlling method for an interventional surgery robot.

BACKGROUND

Nearly 30 million people die from cardiovascular and cerebrovascular diseases every year, accounting for about 30% of all diseases. Among them, nearly 300 million people suffer from cardiovascular and cerebrovascular diseases in China. Cardiovascular and cerebrovascular diseases have become one of the three major causes of death from human diseases, seriously affecting people's health and people's normal lives.

Minimally invasive interventional therapy for cardiovascular and cerebrovascular diseases is the main treatment for cardiovascular and cerebrovascular diseases. Compared with traditional surgery, it has obvious advantages such as small incision and short postoperative recovery time. Cardio-cerebrovascular intervention is a process in which the doctor manually sends catheters, guide wires, and stents into the patient's body to complete the treatment.

Interventional surgery has the following two problems. First, during the operation, the DSA emits X-rays, the doctor's physical strength drop quickly, and the attention and stability will also decrease, which will cause the accuracy of the operation to decrease, and it is prone to cause improper pushing force, resulting to accidents such as vascular intimal damage, vascular perforation and rupture and endangering the lives of the patients. Second, the accumulated damage of long-term ionizing radiation will greatly increase the risk of doctors' suffering from leukemia, cancer, and acute cataracts. The phenomenon that doctors continue to accumulate radiation due to interventional surgery, which damages the professional life of doctors and restricts the development of interventional surgery, has become a problem that cannot be ignored.

The surgical method of teleoperation of catheters and guide wires with the help of robot technology can effectively cope with this problem, and can also greatly improve the accuracy and stability of the surgical operation. At the same time, it can effectively reduce the radiation damage to the interventional doctor and reduce the occurrence of intraoperative accidents. probability. Therefore, assistive robots for cardio-cerebral vascular interventional surgery have attracted more and more attention, and have gradually become the key research and development objects in the field of medical robots in today's scientific and technological powers.

Foreign vascular intervention surgery robots have been studied relatively early, but they have not yet fully achieved clinical applications. Domestic related research started relatively late, mainly including Beijing Institute of Technology, Tianjin University of Technology, Beihang University and Harbin Institute of Technology.

Currently, vascular interventional surgical robots mainly adopt a master-slave operation structure to isolate doctors from radioactivity. For example, the application number of Tianjin University of Technology is: 201410206956.7, and the publication date is: the invention patent on Sep. 17, 2014, which discloses a slave operating device of a master-slave minimally invasive vascular intervention operation auxiliary system. The device includes an axial pushing unit, a rotating unit, a gripping unit, a surgical catheter, an operating force detection unit and an adjustable base. Its working methods include signal detection, transmission, processing, action. The superiority is that it can imitate the interventional operation of the doctor, the operation accuracy is high, and the safety of the operation can be effectively improved. The angle of the intervention position can be adjusted, and the aluminum alloy material is used, which is small in size and light in weight. The invention can well complete the push of the guide wire, and uses magnetorheological fluid to realize force feedback. For another example, the application number of Beijing University of Aeronautics and Astronautics is: 201210510169.2, and the publication date is: Sep. 17, 2014. The patent document discloses a master-slave teleoperation vascular interventional robot. The robot includes a master end control mechanism, a slave end propulsion mechanism and a PMAC controller. The master control mechanism is the operating end of the doctor. The slave propulsion mechanism is used as the actuator of the robot to complete the movement function of the catheter. The PMAC control box is used to realize the interaction between the master control mechanism and the slave propulsion mechanism. It uses master-slave teleoperation to assist doctors in performing operations, and the slave end propulsion mechanism realizes the axial feed and circumferential rotation of the catheter.

However, the above solutions still have the following problems:

(1) The disinfection of the robot is cumbersome and does not meet the actual surgical requirements;

(2) The structure is relatively bloated and complex, large in size, inconvenient to install, and not flexible enough;

(3) The disassembly and assembly of the catheter guide wire is inconvenient, and it is not easy to replace the catheter guide wire during the operation;

(4) It is impossible to advance and rotate the guide wire at the same time. This operation is very practical in actual surgery;

(5) The device is prone to slipping during the advancement of the guide wire, which affects the surgical effect.

Therefore, providing an interventional surgical robot propelling device and a control method thereof that facilitates the control of the movement and rotation of the catheter and the guide wire is an urgent problem for those skilled in the art.

SUMMARY

The present disclosure generally relates to a slave-side propelling device and controlling method for an interventional surgery robot which controls the movement and rotating of the catheter and guide wire.

In order to achieve the above objectives, a slave-side propelling device for an interventional surgical robot is provided. The device includes a transmission part, a sliding part, a pushing part, a rubbing part, a clamping part, a catheter rotating part and a moving stepping motor part.

The rubbing part, the clamping part, the catheter rotating part and the moving stepping motor part are installed and fixed on the housing.

The transmission part is configured to transmit the torque of the moving stepping motor part to the sliding part and the pushing part. The sliding part is configured to drive the guide wire to reciprocate. The pushing part and the clamping part cooperate to clamp or loosen the guide wire. The rubbing part is configured to drive the guide wire to rotate. The catheter rotating part is configured to clamp the catheter and push the catheter into or withdraw the catheter out of the blood vessel.

The device described herein, the slave-side propelling device for an interventional surgery robot can control the propelling and withdrawal of the catheter and guide wire in the vascular intervention operation, as well as the simultaneous rotation of the guide wire, and can realize continuous movement through the structure of reciprocating motion. The operation can be simple and at the same time the control is precise. It can also satisfy the doctor's operation of the guide wire in the vascular interventional operation and achieve the remote control robot to complete the operation, which greatly reduces the risk of receiving more X-rays and protects the doctor's body.

In a preferred embodiment, the transmission part of the slave-side propelling device for an interventional surgical robot described above includes multiple miniature bearings mounted on a connecting member. A long-handled bevel gear and a long-handled spur gear are assembled, fixed, and coaxially mounted on the connecting member. The long-handled bevel gear is meshed with a bevel gear. A short-handled spur gear is mounted on the connecting member through the miniature bearings. The boss of the long-handled spur gear and the short-handled spur gear are respectively connected to a crank connecting rod and a linear connecting rod. The bevel gear and a cam group are fixed by a retaining ring. A through-hole bevel gear meshed with the bevel gear is mounted on the connecting member. When the long-handled bevel gear rotates, it drives the bevel gear to rotate synchronously. The boss parts of the long-handled spur gear and the short-handled spur gear are respectively connected with the crank connecting rod and the linear connecting rod. When the spur gear rotates, the eccentric boss can drive the two connecting rods to make propelling movement, after turning a circle, can achieve a reciprocating movement. When the bevel gear rotates, the cam group will also follow the bevel gear to move synchronously. The through-hole bevel gear rotates, and then drives the bevel gear to follow the rotation; through a series of gear combinations, the rotating force can be transmitted to the place where it is needed.

In a preferred embodiment of the slave-side propelling device for an interventional surgical robot, the crank connecting rod and the linear connecting rod are respectively connected to a distal connecting member and a proximal connecting member. A second linear rail is fixed on the reference surface of the housing. A miniature slider is configured to cooperate with the second linear rail and respectively fixed on the distal connecting member and the proximal connecting member. The slider on a first linear rail is configured to move along the miniature slider. A distal slider connecting member is fixed on the slider of the first linear rail. The upper end of the distal slider connecting member is connected to a narrow slider. A push rod is configured to penetrate the narrow slider. The groove part of the push rod is attached to the cam surface of a cam group. An electromagnet is connected with the narrow slider. The electromagnet is connected to the narrow slider. The electromagnet is energized and can absorb the matched medical rubber block with an iron shell, so that it can contact the guide wire. The electromagnet loses electricity and loses its magnetism, and the medical rubber block can be separated to achieve rapid the effect of separation.

In the preferred embodiment of the slave-side propelling device for an interventional surgical robot, the pushing part can include a left-side bracket and a right-side bracket fixed on the reference surface of the housing. A left small miniature bearing and a right small miniature bearing are configured to respectively pass through the cam group and be fixed on the left-side bracket and the right-side bracket thus reducing the friction during rotation. The cam group can be rotated and used in conjunction with the propelling rod to clamp and open the guide wire.

In the preferred embodiment of the slave-side propelling device for an interventional surgical robot, a third linear rail and a first motor bracket are fixed on the housing. A right-angle connecting plate connected with the slider of the third linear rail is configured to connect with a thread nut passed through by a first stepping motor. Two miniature liner-linear rail and a first slider are mounted on the right-angle connecting plate. A clamping connector is mounted on the first slider and a pinion is rotatably connected to the right-angle connecting plate. The first stepping motor is configured to pass through the pinion. The pinion meshes with the clamping connector. By controlling the forward rotation of the first stepping motor, the two clamping connectors can be driven to move relative to each other, so that the clamping part can be opened, and the first stepping motor can be controlled to rotate in reverse, which can clamp the inner parts of the sterilization box. The extension-shaft can guarantee that the shaft of the first stepping motor is always in the pinion during the vertical movement of the right-angle connecting plate.

In the preferred embodiment of the slave-side propelling device for an interventional surgical robot, a fourth linear rail is fixed on the housing and a slider connector is mounted on a second slider. A second stepping motor is configured to pass through a slider screw connector. A second motor bracket is fixed on the housing and connected to the second stepping motor. By controlling the forward rotation of the second stepping motor, the device can be pushed forward, the guide wire is clamped because the position of the plate that fixed on the guide wire is relatively immobile. By adjusting the number of the second stepping motor's rotation turns, the clamping force of the guide wire can also be adjusted; when controlling the second stepping motor to reverse, the device can be moved backward, which can loosen the guide wire and make it easy to withdraw the guide wire.

In the preferred embodiment of the slave-side propelling device for an interventional surgical robot, a square bracket connector is fixed on the housing and connected to a third stepping motor. The upper-side of the square bracket connector is configured to connect to a fifth linear rail. The upper-side of a third slider mounted on the fifth linear rail is configured to connect to a third motor bracket. A screw nut is configured to pass through the third stepping motor and connect to the third motor bracket. By controlling the forward rotation of the third stepping motor, the third stepping motor can be pushed forward to clamp the catheter. By controlling the reverse rotation of the third stepping motor, the third stepping motor can be pushed to move backwards to loosen the catheter, the catheter can be removed. When cooperate with a sterilization box and the forward rotation of the third stepping motor, the catheter is clamped because of the friction force induced by two friction wheels, and the catheter can be pushed forward and enter the blood vessel. While the third stepping motor reverses, the catheter can be pushed backward and exit the blood vessel.

In the preferred embodiment of the slave-side propelling device for an interventional surgical robot, a sixth linear rail is fixed on the housing. A fourth slider is configured to cooperate with the sixth linear rail. A pillar and a connecting plate are fixed and fastened by a nut. The connecting plate is configured to fixed with a plurality of fourth stepping motors, and one of the fourth stepping motors is configured to match with a screw and pass through the screw nut on the reference surface of the housing, and another fourth stepping motor is configured to pass through the through-hole bevel gear on the reference surface of the housing. Controlling the forward rotation of the fourth stepping motor can make the bevel gear rotate. Because there are two sliders with the medical rubber block, two components can alternately push the guide wire forward, so that the guide wire can be continuously pushed forward into the blood vessels. When the fourth stepping motor is controlled to reverse, the guide wire can be pushed out of the blood vessel continuously. Controlling the third stepping motor to rotate forward can drive the screw to move, and when coordinating the movement of the other side of the rubbing part, the two groups of plates move relatively, which realizes the upward rubbing of the guide wire. Controlling the third stepping motor to reverse can realize the downward movement of the guide wire.

In another aspect, a controlling method of the slave-side propelling device for an interventional surgical robot is provided. The method includes transmitting the torsion force of the moving stepping motor part to the sliding part and the pushing part through the transmission part; the sliding part moves the guide wire back and forth repeatedly, clamping and opening the guide wire through the pushing part and the clamping part cooperatively, thereby driving the movement of the guide wire;

moving the pushing part, the clamping part and the rubbing part up and down repeatedly, thereby driving the guide wire to rotate;

clamping the catheter and rotationally pushing the catheter into or withdrawing it out of the blood vessel through the catheter rotating part.

In the preferred embodiment of controlling method of the slave-side propelling device for an interventional surgical robot, the sliding part is configured to clamp the guide wire by charging the electromagnet, which makes it easy to operate and stable to control.

It can be known from the above technical solutions that, compared with the prior art, the present disclosure provides a slave-side propelling device for an interventional surgical robot and its control method, which has the following beneficial effects:

1. The slave-side propelling device for an interventional surgical robot innovatively adopts a reciprocating mechanical structure design, which greatly reduces the volume of the device.

2. The slave-side propelling device for an interventional surgical robot of the present invention has a simple overall structure, adopts a modular structure design, is easy to disassemble and assemble, has a compact structure, and can be made of plastic, the overall weight is light and the manufacturing cost is low.

3. The reciprocating motion device of the interventional surgery robot of the present invention realizes the clamping of the guide wire. The innovative use of the cam group drives the crank connecting rod structure. The reverse force of the spring can make the push rod tightly attached to the cam surface through. The rotation of the stepping motor realizes the alternate clamping and opening of the guide wire, thereby assisting the completion of the reciprocating movement process.

4. The control method of the reciprocating motion device of the interventional surgical robot of the present invention can realize the clamping, loosening, pushing and retreating of the guide wire by operating the device, which can be operated continuously without switching operations in the middle, which is simple and convenient, and can satisfy all the requirements for guide wires in vascular interventional surgery.

5. The bionic thread rolling structure adopted by the present invention conforms to the actual operating habits of doctors. At the same time, it can also realize the simultaneous completion of the advancing guide wire and the rotating guide wire, which meets the operation requirements in actual surgery.

6. The guide wire and the catheter can be controlled to move at the same time, the action is accurate, and the function of installing the stent can be realized, which meets the operation requirements in the actual operation.

7. The relatively closed structure has better protection for internal motors and other components.

Figure 1:
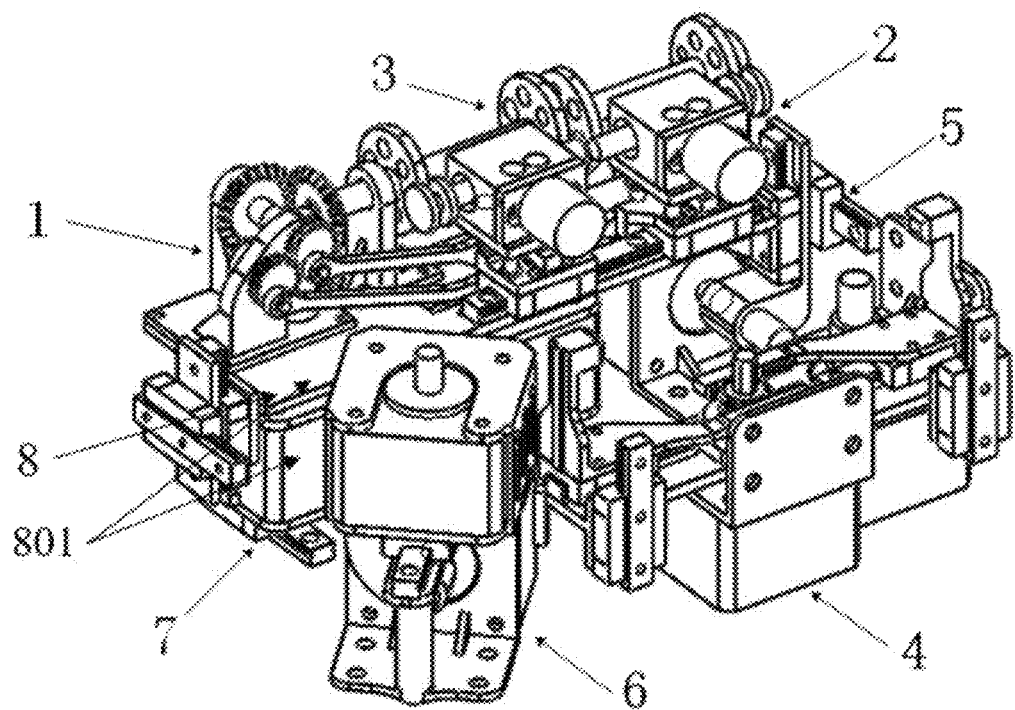
FIG. 1 is a three-dimensional structure diagram of the slave-side propelling device for an interventional surgical robot.

transmission part 1;

connecting member 101; a long-handled bevel gear 102; bevel gear 103; long-handled spur gear 104; short-handled spur gear 105; through-hole bevel gear 106; miniature bearings 107; retaining ring 108;

sliding part 2 crank connecting rod 201; linear connecting rod 202; push rod 203; narrow slider 204; miniature slider 205; distal connecting member 206; proximal connecting member 207; proximal slider connecting member 208; distal slider connecting member 209; first linear rail 210; second linear rail 211; electromagnet 212;

pushing part 3
left-side bracket 301; left small miniature bearings 302; cam group 303; right small miniature bearing 304; right-side bracket 305;
rubbing part 4
first stepping motor 401; first motor bracket 402; third linear rail 403; first slider 404; right-angle connecting plate 405; extension-shaft 406; clamping connector 407; thread nut 408; first screw 409; pinion 410;
clamping part 5
fourth linear rail 501; reference base plate 502; second stepping motor 503; second motor bracket 504; slider connector 505; second slider 506; slider screw connector 507, second screw 508;
catheter rotation part 6
third stepping motor 601; fifth linear rail 602; square bracket connector 603; third slider 604; third motor bracket 605; screw nut 606;
moving stepping motor section 7
sixth linear rail 701; fourth slider 702; fourth stepping motor 703; pillar 704; connecting plate 705; third screw 706; nut 707;

DETAILED DESCRIPTION OF THE EMBODIMENTS

Certain exemplary embodiments will now be described to provide an overall understanding of the principles of the structure, function, manufacture, and use of the instruments and methods disclosed herein. One or more examples of these embodiments are illustrated in the accompanying drawings. Those skilled in the art will understand that the instruments and methods specifically described herein and illustrated in the accompanying drawings are non-limiting exemplary embodiments and that the scope of the present disclosure is defined solely by the claims. The features illustrated or described in connection with one exemplary embodiment may be combined with the features of other embodiments. Such modifications and variations are intended to be included within the scope of the present disclosure.

Embodiment 1

Figure 2:
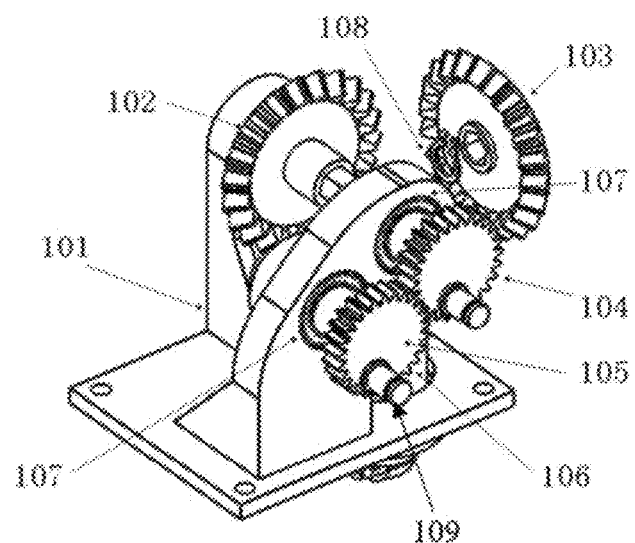
FIG. 2 is a schematic diagram of the transmission part of the slave-side propelling device for an interventional surgical robot.
Figure 3:
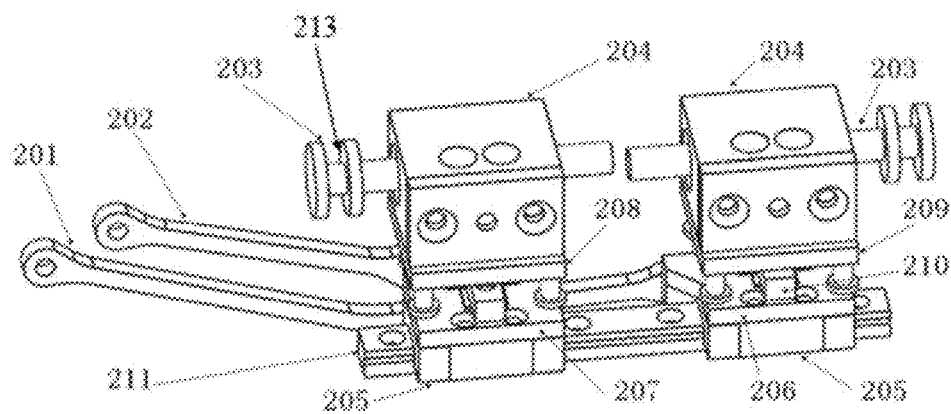
FIG. 3 is a schematic diagram of the sliding part of the slave-side propelling device for an interventional surgical robot.
Figure 4:
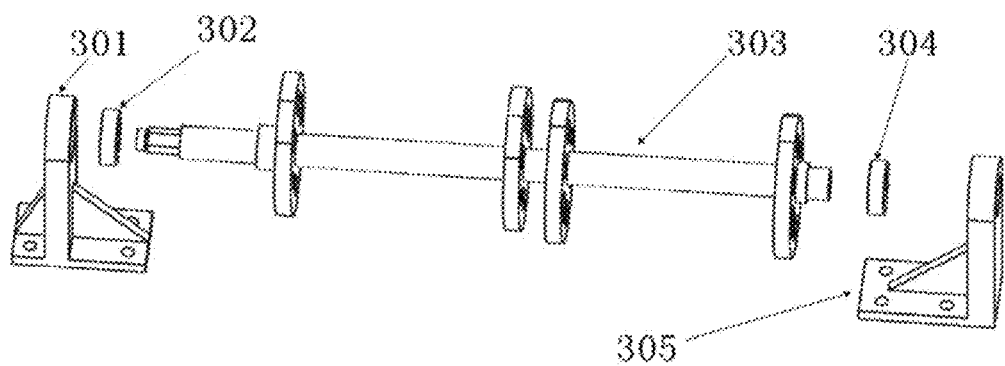
FIG. 4 is an exploded view of the pushing part of the slave-side propelling device for an interventional surgical robot.
Figure 5:
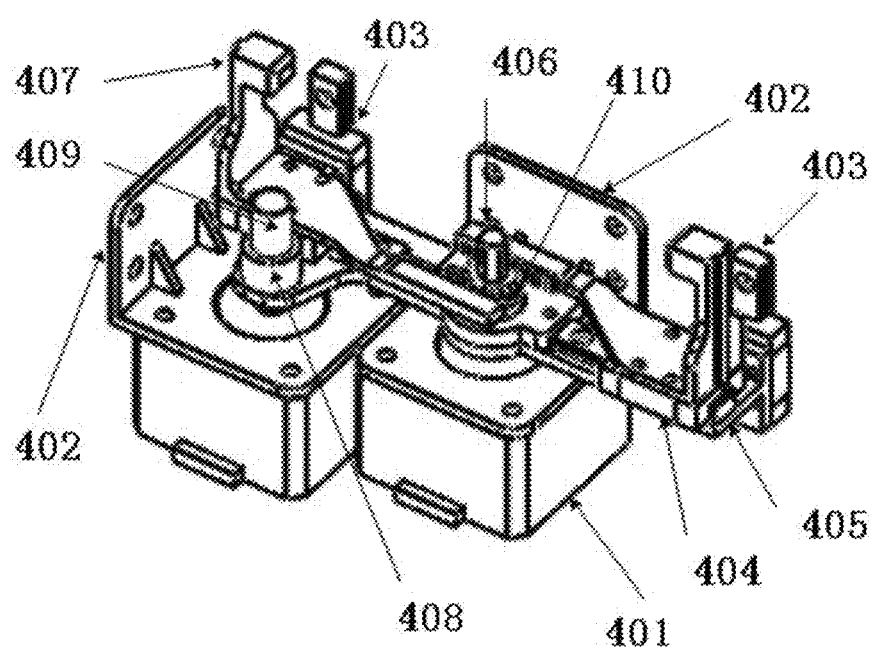
FIG. 5 is a schematic diagram of the rubbing part of the slave-side propelling device for an interventional surgical robot.
Figure 6:
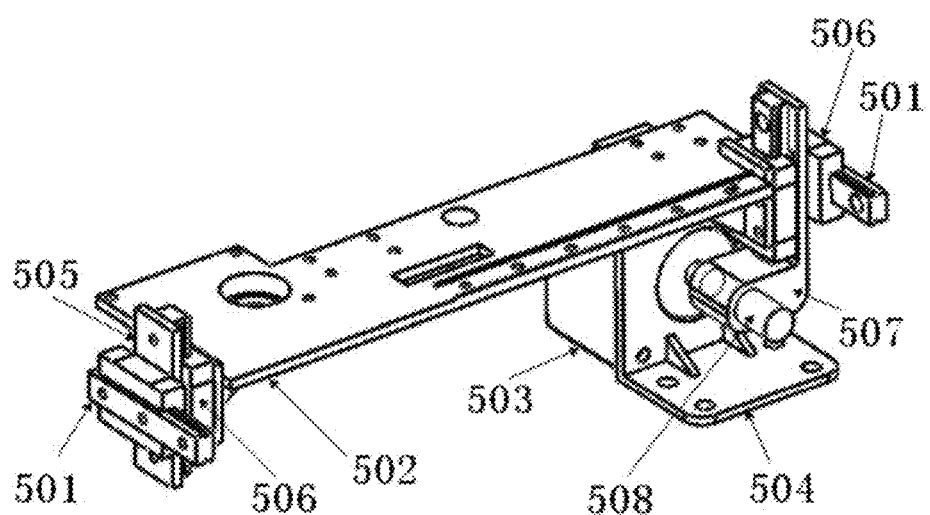
FIG. 6 is a schematic diagram of the clamping part of the slave-side propelling device for an interventional surgical robot.
Figure 7:
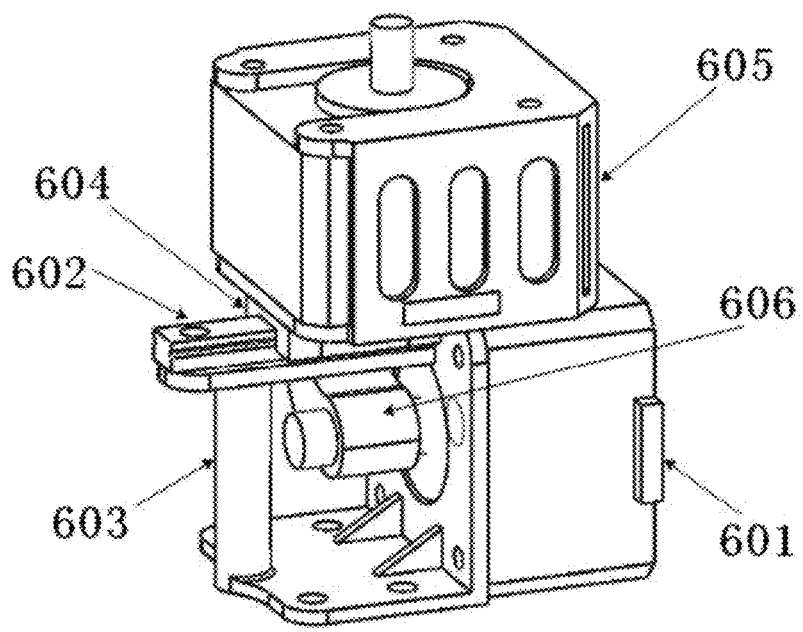
FIG. 7 is a schematic diagram of the structure of the catheter rotation part of the slave-side propelling device for an interventional surgical robot.
Figure 8:
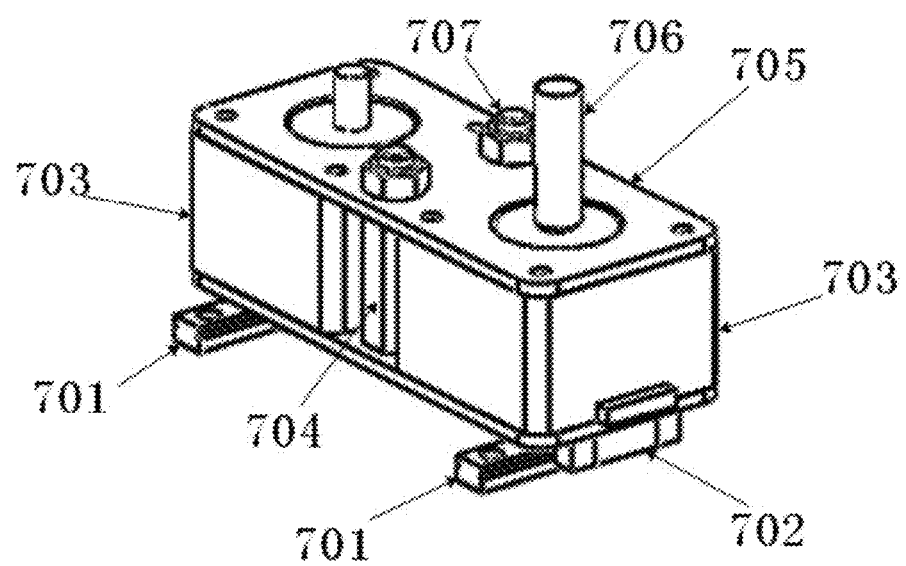
FIG. 8 is a schematic diagram of moving stepping motor section of the slave-side propelling device for an interventional surgical robot.
Figure 9:
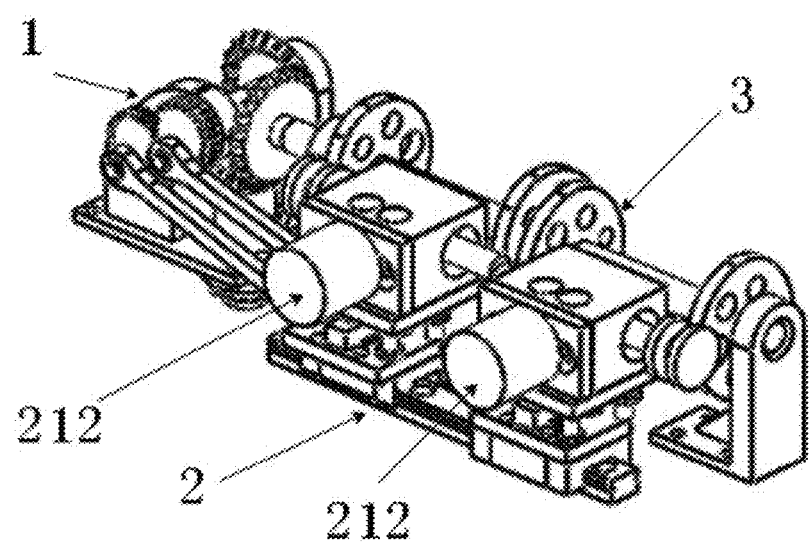
FIG. 9 is the structure diagram of the cooperation of the transmission part, the sliding part and the pushing part.

Referring to FIGS. 1-9, the present disclosure provides a slave-side propelling device for an interventional surgical robot. The device includes a transmission part 1, a sliding part 2, a pushing part 3, a rubbing part 4, a clamping part 5, a catheter rotation part 6 and a moving stepping motor section 7. The rubbing part 4, the clamping part 5, the catheter rotating part 6 and the moving stepping motor part 7 are installed and fixed on the housing. The transmission part is configured to transmit the torque of the moving stepping motor part 7 to the sliding part 2 and the pushing part 3. The sliding part 2 is configured to move guide wire back and forth. The pushing part and the clamping part cooperate to clamp or loosen the guide wire. The rubbing part 4 is configured to drive the guide wire to rotate. The catheter rotating part 6 is configured to clamp the catheter and push the catheter into or withdraw the catheter out of the blood vessel.

For further optimized embodiment, multiple miniature bearings 107 are provided on a connecting member 101. A long-handled bevel gear 102 and a long-handled spur gear 104 are assembled, fixed, and coaxially mounted on the connecting member 101. The long-handled bevel gear 102 is meshed with a bevel gear 103. A short-handled spur gear 105 is mounted on the connecting member 101 through the miniature bearings 107. The boss 109 of the long-handled spur gear 104 and the short-handled spur gear 105 are respectively connected to a crank connecting rod 201 and a linear connecting rod 202. The bevel gear 103 and a cam group 303 are fixed by a retaining ring 108. A through-hole bevel gear 106 meshed with the bevel gear 103 is mounted on the connecting member 101.

For further optimized embodiment, the crank connecting rod 201 and the linear connecting rod 202 are respectively connected to a distal connecting member 206 and a proximal connecting member 207. A second linear rail 211 is fixed on the reference surface 801 of the housing 8, wherein a miniature slider 205 is configured to cooperate with the second linear rail 211 and respectively fixed on the distal connecting member 206 and the proximal connecting member 207. The slider on a first linear rail 210 is configured to move along the miniature slider 205. A distal slider connecting member 209 is fixed on the slider of the first linear rail 210. The upper end of the distal slider connecting member 209 is connected to a narrow slider 204. A push rod 203 is configured to penetrate the narrow slider 204. The groove part 213 of the push rod 203 is attached to the cam surface of a cam group 303. An electromagnet 212 is connected with the narrow slider 204.

For further optimized embodiment, a left-side bracket 301 and a right-side bracket 305 are fixed on the reference surface 801 of the housing 8. A left small miniature bearing 302 and a right small miniature bearing 304 are configured to respectively pass through the cam group 303 and fix on the left-side bracket 301 and the right-side bracket 305.

For further optimized embodiment, a third linear rail 403 and a first motor bracket 402 are fixed on the housing 8. A right-angle connecting plate 405 connected with the slider of the third linear rail 210 is configured to connect with a thread nut 408 passed through by a first stepping motor 401. Two miniature linear rail and a first slider 404 are mounted on the right-angle connecting plate 405. A clamping connector 407 is mounted on the first slider 404 and a pinion 410 is rotatably connected to the right-angle connecting plate 405. The first stepping motor 401 is configured to pass through the pinion 410. The pinion 410 meshes with the clamping connector 407.

For further optimized embodiment, a fourth linear rail 501 is fixed on the housing 8. A slider connector 505 is mounted on a second slider 506. A second stepping motor 503 is configured to pass through a slider screw connector 507. A second motor bracket 504 is fixed on the housing 8 and connected to the second stepping motor 503.

For further optimized embodiment, a square bracket connector 603 is fixed on the housing 8 and connected to a third stepping motor 601. The upper-side of the square bracket connector 603 is configured to connect to a fifth rail 602. The upper-side of a third slider 604 mounted on the fifth linear rail 602 is configured to connect to a third motor bracket 605. A screw nut 606 is configured to pass through the third stepping motor 601 and connect to the third motor bracket 605.

For further optimized embodiment, a sixth linear rail 701 is fixed on the housing 8. A fourth slider 702 is configured to cooperate with the sixth linear rail 701. A pillar and a connecting plate 705 are fixed and fastened by a nut 707. The connecting plate 705 is configured to fixed with multiple fourth stepping motors 703, and one of the fourth stepping motors is configured to match with a third screw 706 and pass through the screw nut on the reference surface 801 of the housing 8, and another fourth stepping motor 703 is configured to pass through the through-hole_bevel gear 106 on the reference surface 801 of the housing 8.

Embodiment 2

A controlling method of the slave-side propelling device for an interventional surgical robot is provided. The method includes transmitting the torsion force of the moving stepping motor part 7 to the sliding part 2 and the pushing part 3 through the transmission part 1. The sliding part 2 drives the guide wire back and forth repeatedly, clamps and opens the guide wire through the pushing part 3 and the clamping part 5 cooperatively, thereby driving the movement of the guide wire;

moving the pushing part 3, the clamping part 5 and the rubbing part 4 up and down repeatedly, thereby driving the guide wire to rotate;

clamping the catheter and rotationally pushing the catheter into or withdrawing it out of the blood vessel through the catheter rotating part 6.

For further optimized embodiment, the sliding part 2 is configured to clamp the guide wire by charging the electromagnet 212.

One skilled in the art will appreciate further features and advantages of the disclosure based on the above-described embodiments. Accordingly, the disclosure is not to be limited by what has been particularly shown and described, except as indicated by the appended claims. All publications and references cited herein are expressly incorporated by reference in their entirety.

What is claimed is:

1. A slave-side propelling device for an interventional surgical robot, comprising: a transmission part, a sliding part, a pushing part, a rubbing part, a clamping part, a catheter rotation part and a driver; wherein the rubbing part, the clamping part, the catheter rotating part and the driver are installed and fixed on a housing; the transmission part is configured to transmit the torque of the driver to the sliding part and the pushing part;

wherein the transmission part further includes a plurality of bearings mounted on a connector; a long-handled bevel gear and a long-handled spur gear with a boss are assembled, fixed, and coaxially mounted on the connector; the long-handled bevel gear is meshed with a bevel gear; a short-handled spur gear with a boss is mounted on the connector through the bearings; the boss of the long-handled spur gear and the short-handled spur gear are respectively and fixedly connected to a crank connecting rod and a linear connecting rod; the bevel gear and a cam group are fixed by a retaining ring; and a through-hole bevel gear meshed with the bevel gear is mounted on the connector;

the crank connecting rod and the linear connecting rod are respectively connected to a distal connector and a proximal connector; a first linear rail is configured on a slider; a second linear rail is fixed on a reference surface of the housing; the slider is configured to cooperate with the second linear rail and fixedly connected with the distal connector and the proximal connector; a distal slider connector is fixedly connected with the first linear rail; the upper end of the distal slider connector is connected to a narrow slider; a push rod is configured to penetrate the narrow slider; a groove part of the push rod fits a cam surface of a cam group; and an electromagnet is connected with the narrow slider;

a left-side bracket and a right-side bracket are fixed on the reference surface of the housing; and a left bearing and a right bearing are configured to respectively pass through the cam group and are fixed on the left-side bracket and the right-side bracket.

2. The device of claim 1, wherein a third linear rail and a first motor bracket are fixed on the housing; a right-angle connecting plate connected with the slider of the third linear rail is configured to connect with a thread nut; a first stepping motor is configured to pass through the thread nut; two linear rails and a first slider are provided on the right-angle connecting plate; a clamping connector is mounted on the first slider; a pinion is rotatably connected to the right-angle connecting plate; the first stepping motor is configured to pass through the pinion; and the pinion connect with the clamping connector.

3. The device of claim 1, wherein a fourth linear rail is fixed on the housing; a slider connector is mounted on a second slider; a second stepping motor is configured to pass through a slider screw connector; and a second motor bracket is fixed on the housing and connected to the second stepping motor.

4. The device of claim 1, wherein a square bracket connector is fixed on the housing and connected to third stepping motor; an upper end of the square bracket connector is configured to connect with a fifth linear rail; the upper end of a third slider mounted on the fifth linear rail is configured to connect with a third motor bracket; and a screw nut is configured to pass through the third stepping motor and connect with the third motor bracket.

5. The device of claim 4, wherein a sixth linear rail is fixed on the housing; a fourth slider is configured to cooperate with the sixth linear rail; a pillar and a connecting plate are firmly connected by a nut; a plurality of driving motors are disposed on the connecting plate; one of the plurality of driving motors is configured to match with a screw, and another one of the plurality of driving motors is configured to pass through the through-hole bevel gear on the reference surface of the housing.

\* \* \* \* \*